(12) United States Patent
Welmaker et al.

(10) Patent No.: US 7,351,839 B2
(45) Date of Patent: Apr. 1, 2008

(54) PROCESS FOR THE PREPARATION OF 1,2,3,4,8,9,10, 10A-OCTAHYDRO-7BH-CYCLOPENTA[B][1,4]DIAZEPINO-[6,7,1-HI]INDOLE DERIVATIVES

(75) Inventors: Gregory S. Welmaker, Collegeville, PA (US); Joan E. Sabalski, Hamilton, NJ (US); Michael D. Smith, Martinez, CA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/602,531

(22) Filed: Nov. 21, 2006

(65) Prior Publication Data

US 2007/0066676 A1    Mar. 22, 2007

Related U.S. Application Data

(62) Division of application No. 10/016,418, filed on Nov. 2, 2001, now Pat. No. 7,141,563.

(60) Provisional application No. 60/245,843, filed on Nov. 3, 2000.

(51) Int. Cl.
*C07D 209/82* (2006.01)
(52) U.S. Cl. .................... 548/448; 548/449
(58) Field of Classification Search ............. 548/448, 548/449
See application file for complete search history.

(56) References Cited

U.S. PATENT DOCUMENTS

| 3,914,250 A | 10/1975 | Kim | 540/556 |
|---|---|---|---|
| 2002/0055504 A1 | 5/2002 | Chan | 514/219 |
| 2002/0055630 A1 | 5/2002 | Welmaker et al. | 540/555 |
| 2002/0062022 A1 | 5/2002 | Sabb et al. | 540/556 |
| 2002/0086860 A1 | 7/2002 | Sabb et al. | 514/219 |
| 2002/0107242 A1 | 8/2002 | Sabb et al. | 514/219 |
| 2002/0119966 A1 | 8/2002 | Sabb et al. | 514/219 |
| 2002/0128261 A1 | 9/2002 | Sabb et al. | 514/219 |

FOREIGN PATENT DOCUMENTS

| WO | WO 96/29316 | 9/1996 |
|---|---|---|
| WO | WO 00/35922 | 6/2000 |
| WO | WO 02/08186 | 1/2002 |

OTHER PUBLICATIONS

Gregory E. Martin et al., J. Med. Chem., 32, 1052-1056 (1989).
J.L. Browning et al., Society for Neuroscience Abstracts, Oct. 1999, 2075, 25(2), Abstract 830.12.
Jackson B. Hester et al., J. Med. Chem., 13, 827-835 (1970).
H.P. Haerter et al., Chimia, 30, 50-52 (1976).
D. Kim, J. Heterocyclic Chem., 13, 1187-1192 (1976).
S. Archer et al., J. Am. Chem. Soc., 79, 5783-5785 (1957).
L. Zhang et al., Tetrahedron Letters, 36(46), 8387-8390 (1995).
G.E. Stokker, Tetrahedron Letters, 37(31), 5453-5456 (1996).
Cuadro et al., Synthetic Communications, 21(4), 535-544 (1991).
W. Perkin et al., J. Chem. Soc., 123, 3242-3247 (1923).
H. Booth et al., J. Chem. Soc., 158, 2302-2311 (1958).
Gregory S. Welmaker et al., Tetrahedron Letters, 45, xxx-xxx (2004) (4 pages).

*Primary Examiner*—Brenda Coleman
(74) *Attorney, Agent, or Firm*—Kimberly R. Hild

(57) ABSTRACT

This invention provides processes for preparing compounds formula:

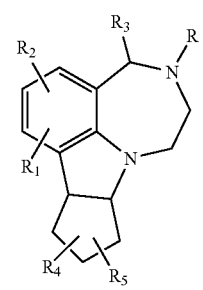

wherein R is H, alkyl, acyl, aryl, aroyl or —C(O)R'; R' is alkyl or aryl; $R_1$, $R_2$, $R_4$ and $R_5$ are H, —OH, alkyl, cycloalkyl, alkoxy, halogen, fluorinated alkyl or alkoxy, —CN, —NH—$SO_2$-alkyl, —$SO_2$—NH-alkyl, alkyl amide, amino, alkylamino, dialkylamino, acyl, aryl or aroyl; $R_3$ is H, alkyl, cycloalkyl, alkoxy, fluorinated alkyl, —NH—$SO_2$-alkyl, —$SO_2$—NH-alkyl, alkyl amide, amino, alkylamino, dialkylamino, fluorinated alkoxy, acyl, aryl, or aroyl; or a pharmaceutically acceptable salt thereof, as well as novel compounds useful in the synthesis of these compounds.

12 Claims, No Drawings

PROCESS FOR THE PREPARATION OF 1,2,3,4,8,9,10, 10A-OCTAHYDRO-7BH-CYCLOPENTA[B][1,4]DIAZEPINO-[6,7,1-HI]INDOLE DERIVATIVES

This application is a divisional of U.S. application Ser. No. 10/016,418 filed on Nov. 2, 2001, now U.S. Pat. No. 7,141,563 which in turn claims the benefit of U.S. Provisional Application No. 60/245,843, filed Nov. 3, 2000. The entire disclosures of the 10/106,418 application and 60/245,843 application are hereby incorporated by reference.

The present invention relates to a process for the preparation of 1,2,3,4,8,9, 10, 10a-octahydro-7bH-cyclopenta[b][1,4]diazepino[6,7,1-hi]indole derivatives, which are useful for the treatment and prevention of central nervous system disorders, including obsessive-compulsive disorder, depression, anxiety, generalized anxiety disorder, schizophrenia, panic disorder, migraine, sleep disorders, such as sleep apnea, eating disorders, such as hyperphagia, obesity, epilepsy, and spinal cord injury. This invention also provides novel compounds useful as intermediates in the synthesis of these pharmaceutical agents.

BACKGROUND OF THE INVENTION

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the 21$^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J.) 147-210 (Wiley-Liss, New York, 1991).] The 5HT$_{2C}$ receptor (formerly called the 5HT$_{1C}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558-564 (1988).] Studies in several animal species and in humans have shown that the non-selective 5HT$_{2C}$ receptor agonist, meta-chlorophenylpiperazine (MCPP) decreases food intake. [Cowen, P. J., Clifford, E. M., Williams, C., Walsh, A. E. S., Fairburn, C. G. *Nature* 376: 557 (1995).] Tecott, et al have demonstrated that transgenic mice lacking the 5HT$_{2C}$ receptor eat more and are heavier than Wild Type mice. [Tecott, L. H., Sun, L. M., Akana, S. F., Strack, A. M., Lowenstein, D. H., Dallman, M. F., Jullus, D. *Nature* 374: 542-546 (1995).] Compounds of this invention are 5HT$_{2C}$ receptor subtype selective agonists which are selective over other monoamine receptors, causes a reduction in food intake and result in a reduction in weight gain. Other therapeutic indications for 5HT$_{2C}$ agonists are obsessive compulsive disorder, depression, panic disorder, schizophrenia, sleep disorders, eating disorders, and epilepsy.

The non-selective 5-HT$_{2c}$ agonist, meta-chlorophenylpiperazine (m-CPP), has been shown to block conditioned avoidance responding (CAR) in the rat, an activity usually associated with antipsychotic activity in man [Martin, Gregory E.; Elgin, Jr., Robert J.; Mathiasen, Joanne R.; Davis, Coralie B.; Kesslick, James M.; Baldy, William J.; Shank, Richard P.; DiStefano, Deena L.; Fedde, Cynthia L.; Scott, Malcolm K. *J. Med. Chem.* 1989, 32, 1052-1056]. More recently, additional data suggests that 5-HT$_{2c}$ agonism may produce an antipsychotic-like effect in the CAR model [Browning, J. L.; Young, K. A.; Hicks, P. B. Presented at the 29$^{th}$ Annual Meeting of the Society for Neuroscience, Miami Beach, Fla., October 1999, Abstract 830.12].

U.S. Pat. No. 3,914,250 (Oct. 21, 1975) describes 1,4-diazepino[6,5,4-jk]carbazoles as anticonvulsant agents.

Pyrrolo[3,2,1-jk][1,4]benzodiazepines and 4,5-dihydro-pyrrolo[3,2,1-jk][1,4]-benzodiazepines have been described by Hester et al. (*J. Med. Chem.* 1970, 13, 827-835) to have central nervous system activity.

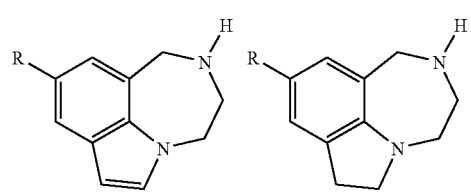

In 1975, Dong H. Kim described 1,4-diazepino[6,5,4-jk] carbazoles (U.S. Pat. No. 3,914,250) and their utility as anticonvulsants.

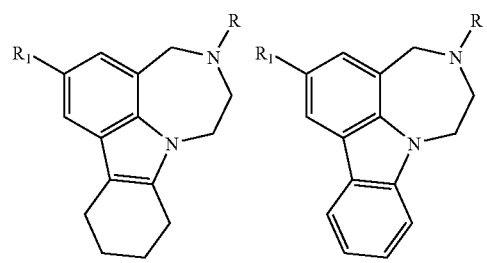

DESCRIPTION OF THE INVENTION

The present invention relates to a process for the preparation of 1,2,3,4,8,9, 10,10a-octahydro-7bH-cyclopenta[b][1,4]diazepino[6,7,1-hi]indole derivatives of the general formula:

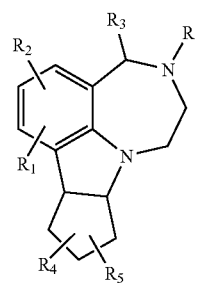

I wherein

R is hydrogen, alkyl of 1-6 carbon atoms, aryl, aroyl or —C(O)R';

R' is alkyl of from 1 to 6 carbon atoms or aryl, preferably phenyl;

R$_1$, R$_2$, R$_4$ and R$_5$ are each, independently, hydrogen, hydroxy, alkyl of 1-6 carbon atoms, cycloalkyl, alkoxy of 1-6 carbon atoms, halogen, fluorinated alkyl of from 1 to 6 carbon atoms, —CN, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl or aroyl;

R$_3$ is hydrogen, alkyl of 1-6 carbon atoms, cycloalkyl, alkoxy of 1-6 carbon atoms, fluorinated alkyl of from 1 to 6 carbon atoms, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl, or aroyl;

or a pharmaceutically acceptable salt thereof.

The compounds of this invention may contain an asymmetric carbon atom and some of the compounds of this invention may contain one or more asymmetric centers and may thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

In the definitions herein, the fluorinated alkyl and fluorinated alkoxy groups indicate the specified alkyl or alkoxy groups having any amount of fluorine substitution including, but not limited to, groups such as —CHF$_2$, —CF$_3$, —C$_2$F$_5$, —OCF$_3$, etc.

The term "alkyl" includes both straight- and branched-chain saturated aliphatic hydrocarbon groups. The term "aroyl" is defined as an aryl ketone, where aryl is defined as an aromatic system of 6-14 carbon atoms, which may be a single ring or multiple aromatic rings fused or linked together as such that at least one part of the fused or linked rings forms the conjugated aromatic system. Preferred aryl groups include phenyl, naphthyl, biphenyl, anthryl, tetrahydronaphthyl, phenanthryl groups. Halogen is defined as F, Cl, Br, and I.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Each of the processes described herein are understood to include an additional optional step in which a compound of Formula I is treated with the relevant pharmaceutically acceptable addition inorganic or organic acid to produce the corresponding pharmaceutically acceptable salt form.

One group of preferred compounds prepared by the processes of this invention are those in which R is hydrogen. Another group of compounds include those in which R$_3$ is H, R is H or alkyl of from 1 to 6 carbon atoms, R$_1$, R$_2$, R$_4$ and R$_5$ are as defined above. In another group, R and R$_3$ are H and R$_1$, R$_2$, R$_4$ and R$_5$ are as defined above. In a further group, R, R$_1$, R$_2$, R$_3$ and R$_4$ are H and R$_5$ is as defined above.

The 5HT$_{2C}$ receptor agonists of this invention are useful for the treatment or prevention in mammals, preferably in humans, of disorders involving the central nervous system such as obsessive-compulsive disorder, depression, atypical depression, bipolar disorders, anxiety, generalized anxiety disorder, schizophrenia, psychoses, personality disorders, organic mental disorders, behavioral disorders associated with dementia or age-related conditions, aggressivity, drug and alcohol addiction, social phobias, sexual dysfunction, panic disorder, migraine, sleep disorders, such as sleep apnea, eating disorders, such as hyperphagia, bulimia or anorexia nervosa, obesity, epilepsy, and premenstrual tension.

The compounds herein may also be used in treatments or preventative regimens for treatment of central nervous system deficiencies associated with trauma, stroke, neurodegenerative diseases or toxic or infective CNS disorders including, but not limited to, encephalitis or menengitis; or cardiovascular disorders, including thrombosis; gastrointestinal disorders such as malfunction of gastrointestinal motility; and diabetes insipidus. These methods include the improvement or inhibition of further degradation of central nervous system activity during or following the malady or trauma in question. Included in these improvements are maintenance or improvement in motor and motility skills, control, coordination and strength.

This invention provides a process for synthesis of a compound of the formula:

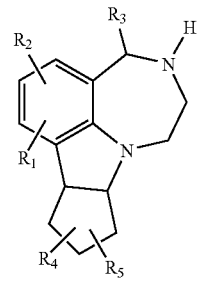

wherein R, R$_1$, R$_2$, R$_3$, R$_4$ and R$_5$ are as defined above, the process comprising the steps of:

a) converting a cyclopenta[b]indole compound of the formula:

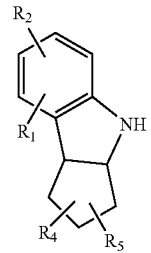

to an optionally substituted cyclopenta[b]indol-4-ylacetamide compound of the formula:

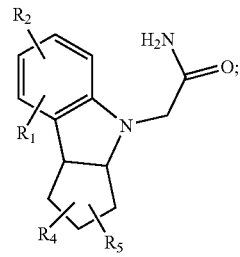

b) reducing the optionally substituted cyclopenta[b]indol-4-ylacetamide of step a) to the corresponding optionally substituted cyclopenta[b]indol-4-yl-amine of the formula:

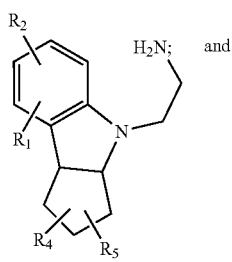 and c) cyclizing the cyclopenta[b]indol-4-yl-amine of step b) to an optionally substituted diaza-benzo[cd]cyclopenta[a]azulene compound of the formula:

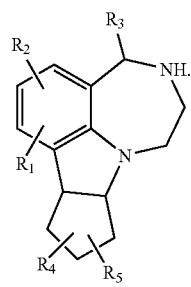

The process above further optional comprises an initial step wherein the cyclopenta[b]indole compound of step a) is formed from the reduction of a cyclopenta[b]indole compound of the formula:

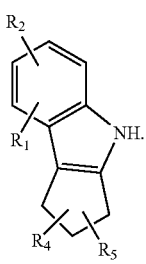

This process further comprises the optional steps of alkylating or acylating the final optionally substituted diaza-benzo[cd]cyclopenta[a]azulene compound above to produce a compound of the formula:

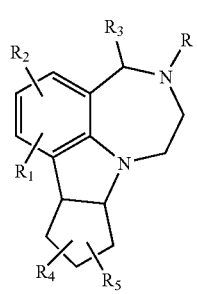

wherein R is as defined above.

An alternate synthesis of this invention comprises the steps of:

a) converting an optionally substituted cyclopenta[b]indole compound of the formula:

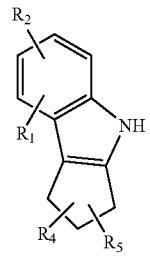

to produce an optionally substituted nitrile compound of the formula:

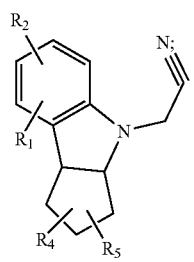

b) reducing the optionally substituted nitrile compound of step a) to provide an optionally substituted amine compound of the formula:

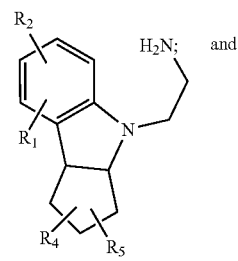 and c) cyclizing the amine compound of step b) to an optionally substituted diaza-benzo[cd]cyclopenta[a]azulene compound of the formula:

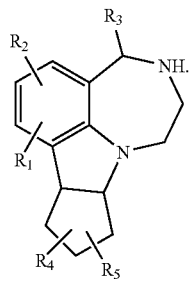

This alternate process further comprises the optional steps of alkylating or acylating the final optionally substituted diaza-benzo[cd]cyclopenta[a]azulene compound above to produce the corresponding N-alkylated or acylated compounds, as defined above.

In Scheme I and in the following description and examples the process steps are explained in detail. An arylhydrazine II is allowed to react with a ketone III under standard Fischer-indole conditions. The reaction is carried out in the presence of an acid, such as sulfuric acid or acetic acid, with or without a solvent, such as water or ethanol, at a temperature above ambient temperature, such as 30-150° C.

The resulting indole IV can be reduced to indoline V by catalytic hydrogenation in the presence of a metal catalyst, such as 5% Pd/C or by a hydride source, such as triethylsilane or borane, in the presence of an acid, such as trifluoroacetic acid.

The indoline V can be coupled with an appropriate electrophile, such as chloroacetamide, or a corresponding synthetic equivalent, in the presence of a base, such as diisopropylethylamine or potassium hydroxide, in a suitable solvent, such as DMF or DMSO to give the amide VI.

The amide VI can be reduced to the amine VIII with a reducing agent, such as borane or lithium aluminum hydride, in the presence of an inert organic solvent, such as tetrahydrofuran.

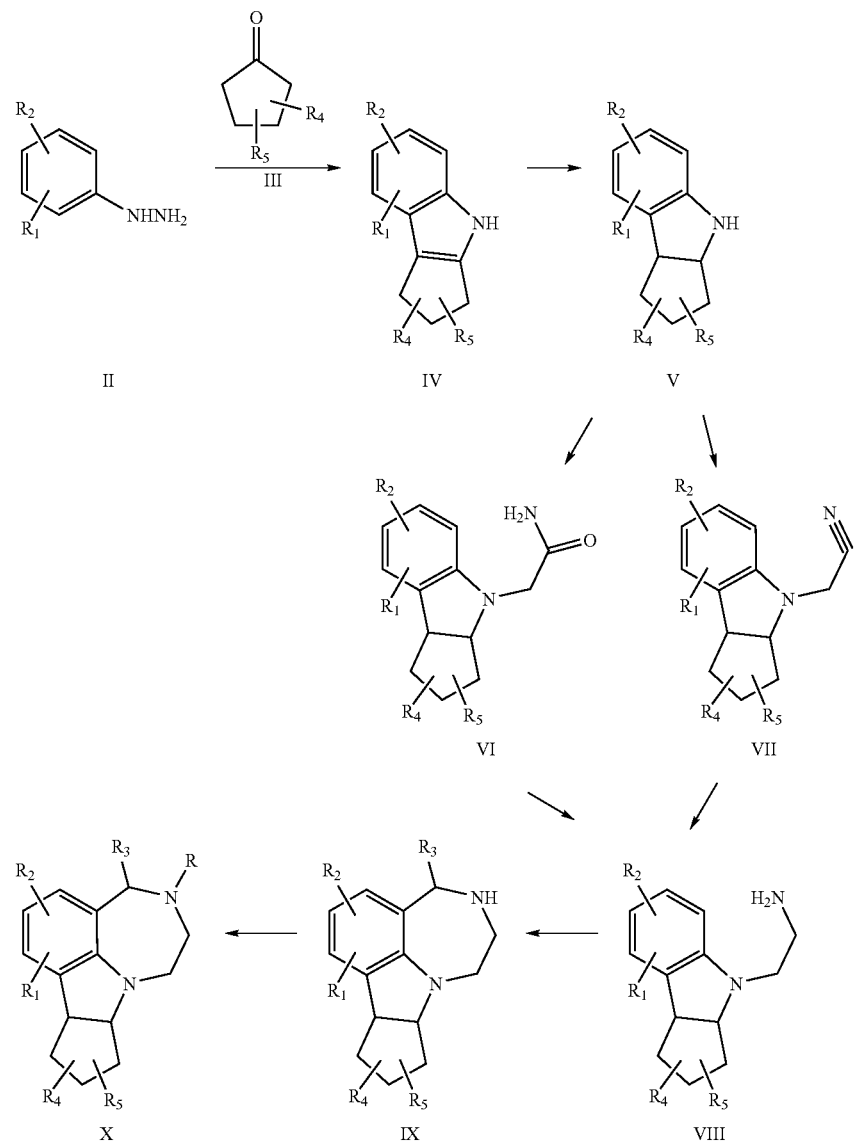

In another process of this invention, indoline V can be coupled with an appropriate electrophile, such as chloroacetonitrile, or a corresponding synthetic equivalent, in the presence of a base, such as diisopropylethylamine or sodium hydride, in a suitable solvent, such as DMF or DMSO to give the nitrile VII.

The nitrile VII can be reduced to the amine VIII with a reducing agent, such as borane or lithium aluminum hydride, in the presence of an inert organic solvent, such as tetrahydrofuran. The nitrile VII can also be reduce to the amine VIII by hydrogenation in the presence of a catalyst, such as palladium, in a suitable solvent, such as ethanol or ethyl acetate.

The amine VIII can be cyclized to the benzodiazepine IX by treatment with one equivalent of an aldehyde, such as formaldehyde or acetaldehyde, in the presence of an acid, such as trifluoroacetic acid, in a suitable solvent, such as ethanol, at room temperature or elevated temperatures.

Reaction of benzodiazepine IX with an alkyl halide, such as methyl iodide, or an acyl halide, such as acetyl chloride, or an aroyl chloride, such as benzoyl chloride, gives X.

The acylation steps of this invention are understood to include reactions of the appropriate compound with any acylating agent and reaction conditions known in the art. Useful in these steps are acylating agents include acid halides and esters or anhyrides of the appropriate aliphatic carboxylic acid. Useful acid halides include acetyl chloride, propionyl chloride, isobutyryl chloride, benzoyl chloride, etc. Acid anhydrides include acetic anhydride and benzoic anhydride. Similarly, alkylation steps herein are understood to include any relevant alkylating agents and conditions known in the art. These include, but are not limited to the use of alkyl halides, such as methyl iodide, or alkyl tosylates or aldehyde alkylating agents in the presence of an applicable reducing agent. It will also be understood that the reduction steps of the processes herein may be accomplished by treatment with reducing agents and conditions known in the art.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids. The processes herein will be understood to include an optional additional step of forming a salt form of the products via standard addition reactions with any pharmaceutically acceptable organic or inorganic acid.

This invention also provides novel groups of compounds useful in the synthesis of the pharmaceutically useful compounds of Formula I. These compounds are of the general formula:

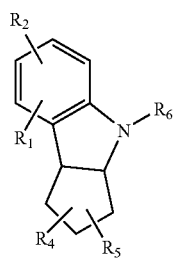

wherein $R_6$ is —$CH_2$—C(O)—$NH_2$, —$CH_2$—CN or —$CH_2$—$CH_2$—$NH_2$; and $R_1$, $R_2$, $R_4$ and $R_5$ are as defined herein.

One group of compounds provided by this invention are optionally substituted cyclopenta[b]indol-4-yl-acetamide compounds of the formula VI:

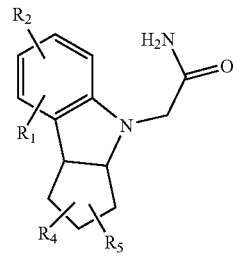

wherein $R_1$, $R_2$, $R_4$ and $R_5$ are each, independently, hydrogen, hydroxy, alkyl of 1-6 carbon atoms, cycloalkyl, alkoxy of 1-6 carbon atoms, halogen, fluorinated alkyl of from 1 to 6 carbon atoms, —CN, —NH—$SO_2$-alkyl of 1-6 carbon atoms, —$SO_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl or aroyl. A subset of these compounds includes those in which $R_1$ and $R_2$ are hydrogen, and $R_4$ and $R_5$ are as defined above. A further subset of these compounds are those in which $R_1$, $R_2$ and $R_4$ are hydrogen, and $R_5$ is as defined above. A preferred specific compound of this group is 2-(2,3,3a,8b-Tetrahydro-1H-cyclopenta[b]indol-4-yl)-acetamide, in which each of $R_1$, $R_2$, $R_4$ and $R_5$ are hydrogen.

Another group of compounds provided by this invention are optionally substituted cyclopenta[b]indol-4-yl-acetonitrile compounds of the formula:

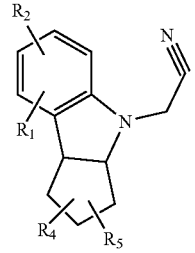

wherein $R_1$, $R_2$, $R_4$ and $R_5$ are as defined for the compounds of Formula VI, above. A subset of these compounds includes those in which $R_1$ and $R_2$ are hydrogen, and $R_4$ and $R_5$ are as defined above. A further subset of these compounds are those in which $R_1$, $R_2$ and $R_4$ are hydrogen, and $R_5$ is as defined above. A preferred specific compound of this group is 2-(2,3,3a,8b-Tetrahydro-1H-cyclopenta[b]indol-4-yl)-acetonitrile, in which each of $R_1$, $R_2$, $R_4$ and $R_5$ are hydrogen.

A further group of compounds provided by this invention are optionally substituted cyclopenta[b]indol-4-yl-ethylamine compounds of the formula:

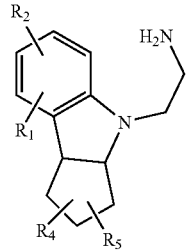

wherein $R_1$, $R_2$, $R_4$ and $R_5$ are as defined for the compounds of Formulas VI and VI, above. A subset of these compounds includes those in which $R_1$ and $R_2$ are hydrogen, and $R_4$ and $R_5$ are as defined above. A further subset of these compounds are those in which $R_1$, $R_2$ and $R_4$ are hydrogen, and $R_5$ is as defined above. A preferred specific compound of this group is 2-(2,3,3a,8b-Tetrahydro-1H-cyclopenta[b]indol-4-yl)-ethylamine, in which each of $R_1$, $R_2$, $R_4$ and $R_5$ are hydrogen.

An alternate synthetic route within the scope of this invention is indicated by Scheme 2, which shares the initial and final steps disclosed in Scheme 1. In this method, rather than reducing the indole IV to indoline V, as done in Scheme 1, the indole IV is directly converted to the corresponding amide XI or nitrile XII, which can then be reduced to the corresponding amines XIII and VIII.

A method of resolving the (R,R) enantiomer from racemic mixtures of these compounds comprises the steps of:

a) dissolving about 1 equivalent of the racemic compound mixture of a product of this invention in a solubilizing amount of an alcohol resolving agent at a temperature of from about 50° C. to the reflux temperature for the alcohol, preferably between about 50° C. and 70° C., under an inert atmosphere, to create a resolving solution;

b) treating the resolving solution of step a) with from about 0.1 to about 0.35 equivalents of dibenzoyl-L-tartaric acid, preferably from about 0.15 equivalents to about 0.3 equivalents, more preferably from about 0.23 to about 0.27 equivalents, most preferably about 0.25 equivalents to precipitate the desired (R,R) enantiomer from the resolving solution as the corresponding tartaric acid salt form; and c) separating the desired enantiomer from the resolving solution through conventional means, such as filtration.

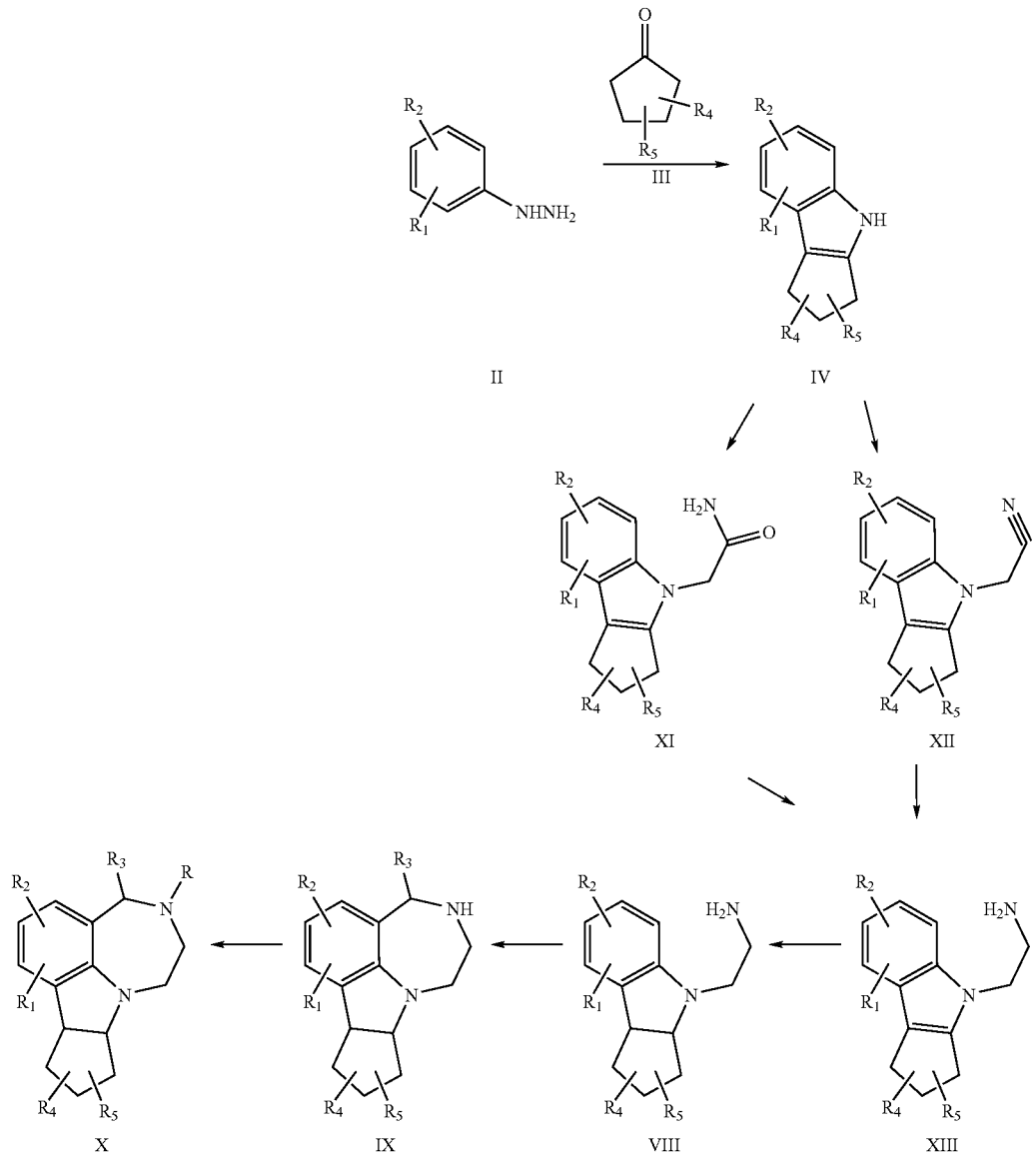

Scheme 2

It will be understood that this process may be followed by additional steps of filtration and purification to enhance the purity and yield of the desired enantiomer product in question.

In step b) it is preferred that the temperature of the resolving solution be maintained at a temperature at or above about 50° C., preferably nearer to the reflux temperature of the alcohol in question. The alcohol component of step a) may be comprise a single alcohol or a combination of two or more alcohols selected from those known in the art into which the compound in question can be dissolved. Among the preferred alcohols are the commercially available and relatively low boiling alcohols comprising 10 carbon atoms or less including methanol, ethanol, n-propanol, isopropanol, n-butanol, t-butanol, cyclohexanol, etc.

It will also be understood that the (S,S) enantiomer of the racemic mixture mentioned above could then be purified and collected from the remaining resolving solution described above after collection of the (R,R) tartaric acid salt.

An analogous method for resolving the (S,S) enantiomer from the racemic mixtures of compounds of this invention, the method comprising the steps a) through c) listed above, with dibenzoyl-D-tartaric acid being used in place of dibenzoyl-L-tartaric acid in step b). Comparably, the (R,R) enantiomer can be collected and purified by conventional means from the remaining solution after the tartaric acid salt form of the (S,S) enantiomer is precipitated and removed in this analogous method.

The following examples illustrate the present invention in more detail; however, they are not intended to limit its scope in any manner.

EXAMPLE 1

1,2,3,4,8,9,10,10a-Octahydro-7bH-Cyclopenta[b][1,4]Diazepino[6,7,1-hi]Indole

A. 1,2,3,4-Tetrahydrocyclopenta[b]Indole

Concentrated sulfuric acid (~18 M, 35 mL) was added dropwise to a mixture of phenyl hydrazine (510 mmol, 50 mL) and cyclopentanone (45 mL, 510 mmol) in water (250 mL). The resulting mixture was heated to reflux for 30 min and then allowed to cool to room temperature. The liquid was decanted from the reaction mixture leaving a red, gummy solid. Hexanes (500-600 mL) was added to the flask and the mixture was heated to reflux. The yellow hexane solution was decanted hot from the mixture and placed in the freezer (crystallization begins immediately). More hexanes is added to the flask and the procedure repeated two more times using a total volume of 1500 mL of hexanes. After 1 h in the freezer, the solid was collected from the flasks and dried providing the known indole (410 mmol, 65 g, 80%).
Anal. Calcd. for $C_{11}H_{11}N$: C, 84.04; H, 7.05; N, 8.91
Found: C, 83.92; H, 7.12; N, 8.85

B. 1,2,3,3a,4,8b-Hexahydrocyclopenta[b]Indole

A mixture of 1,2,3,4-tetrahydrocyclopenta[b]indole (11 mmol, 1.8 g), 5% Pd/C (0.5 g), and concentrated hydrochloric acid (1.2 mL) was hydrogenated at 45 psi on a Parr shaker. After 3 h, the mixture was removed from the shaker and filtered through Celite. The solid bed was washed with methanol. The filtrate was concentrated. The crude oil was dissolved in 1 N HCl and washed with ether. The aqueous phase was treated with 2.5 N NaOH to pH>10 and then extracted with chloroform. The combined chloroform extracts were dried over $MgSO_4$, filtered and concentrated to give the crude indoline. The material was purified by flash column chromatography through silica gel (Biotage, elution with 10% ethyl acetate-hexanes) to give the known indoline (7.6 mmol, 1.2 g, 69%) as a clear oil.
Anal. Calcd. for $C_{11}H_{13}N$: C, 82.97; H, 8.23; N, 8.80
Found: C, 82.61; H, 8.35; N, 8.72

C. 2-(2,3,3a,8b-Tetrahydrocyclopenta[b]Indol-4(1H)-yl)Acetamide

To a stirred solution of 1,2,3,3a,4,8b-hexahydrocyclopenta[b]indole (130 mmol, 21 g) in DMF (50 mL) was added diisopropylethylamine (400 mmol, 70 mL) followed by 2-chloroacetamide (270 mmol, 25 g). The reaction mixture was heated to 100° C. for 18 h. The reaction was concentrated and the diluted with ethyl acetate and water. The phases were separated and the organic phase was washed with brine, dried over $MgSO_4$, filtered and concentrated. The crude material was purified by flash column chromatography through silica gel (elution with 60% ethyl acetate-hexanes) to afford a yellow solid (90 mmol, 20 g, 69%).
Anal. Calcd. for $C_{13}H_{16}N_2O$: C, 72.19; H, 7.46; N, 12.95.
Found: C, 72.45; H, 7.57; N, 12.64.
MS ((+)APCI, m/e(%)) 217(100, [M+H]$^+$).
IR (solid ATR, cm$^{-1}$) 3450, 2930, 2870, 1680, 1480, 1150, 740.
$^1$H NMR (DMSO-d$_6$, 400 MHz) δ 7.20(s,1H), 7.05(s, 1H), 6.90(m, 2H), 6.48(dt, J=0.73 Hz, 7.3 Hz, 1H), 6.18(d, J=7.8 Hz, 1H), 4.22(m, 1H), 3.70, 3.58(ABq, J$_{AB}$=17.1 Hz, 2H), 3.64(m, 1H), 1.90(m, 1H), 1.78(m, 1H), 1.56(m, 3H), 1.40(m, 1H).

D. 2-(2,3,3a,8b-Tetrahydrocyclopenta[b]Indol-4(1H)-yl)Acetonitrile

To a stirred solution of 1,2,3,3a,4,8b-hexahydrocyclopenta[b]indole (22 mmol, 3.5 g) in DMSO (44 mL) was added 60% sodium hydride (24 mmol, 0.97 g) portionwise, followed by 2-chloroacetonitrile (33 mmol, 2.1 mL). The reaction mixture stirred at ambient temperature for 18 h and then additional 60% sodium hydride (22 mmol, 0.88 g) and 2-chloroacetonitrile (24 mmol, 1.5 mL) was added. The reaction was heated to 60° C. for 18 h. The reaction was concentrated and the diluted with ethyl acetate and water. The phases were separated and the organic phase was washed with brine, dried over $MgSO_4$, filtered and concentrated. The crude material was purified by flash column chromatography through silica gel (elution with 60% ethyl acetate-hexanes) to afford the desired material.
$^1$H NMR (DMSO-d$_6$, 400 MHz) δ 7.25(s, 1H), 7.05(m, 1H), 6.78(m, 1H), 6.46(m, 1H), 4.30-3.70(m, 4H), 2.10-1.50 (m, 6H).
MS ((−)APCI, m/e(%)) 198(40, [M]).

E. 2-(2,3,3a,8b-Tetrahydrocyclopenta[b]Indol-4(1H)-yl)Ethylamine 2-(2,3,3a,8b-Tetrahydrocyclopenta[b]indol-4(1 h)-yl)acetamide (90 mmol, 20 g) was dissolved in 1 M BH$_3$.THF (200 mL) and heated to reflux for 18 h. The reaction mixture was allowed to cool to room temperature and then quenched slowly with methanol. The solution was concentrated, dissolved in methanol, and again concentrated. The resulting oil was diluted with ether and extracted twice with 1 N HCl. The aqueous phase was treated with 2.5 N NaOH to pH>10 and extracted with chloroform. The combined chloroform extracts were dried over MgSO$_4$, filtered and concentrated to provide a yellow oil.

Anal. Calcd. for C$_{13}$H$_{18}$N$_2$. 0.55 mol H$_2$O: C, 73.58; H, 9.07; N, 13.20.

Found: C, 73.62; H, 8.80; N, 12.83.

MS (EI, m/e(%)) 202(10, M$^+$), 172(100), 130(20).

IR (film ATR, cm$^{-1}$) 2950, 2870, 1605, 1480, 1250(br), 730.

$^1$H NMR (DMSO-d$_6$, 400 MHz) δ 6.89(dd, J=0.73 Hz, 7.3 Hz, 2H), 6.42(dt, J=0.73 Hz, 7.3 Hz, 1H), 6.29(d, J=7.6 Hz, 1H), 4.12(m, 1H), 3.62(dt, J=2.4 Hz, 9.0 Hz, 1H), 3.08(m, 2H), 2.65(m, 2H), 1.90(m, 1H), 1.75(m, 1H), 1.58(m, 3H), 1.43(m, 1H).

F. 1,2,3,4,8,9,10,10a-Octahydro-7bH-Cyclopenta[b][1,4]Diazepino[6,7,1-hi]Indole

A solution of 2-(2,3,3a,8b-tetrahydrocyclopenta[b]indol-4(1H-yl)ethylamine (25 mmol, 5.0 g) was dissolved in ethanol (125 mL) at room temperature and trifluoroacetic acid (25 mmol, 1.9 mL) was added, followed by aqueous formaldehyde (25 mmol, 37%, 1.9 mL). The reaction was heated to reflux for one hour and an aliquot was removed, concentrated and an NMR taken, which showed the reaction complete. The reaction vessel was cooled and then concentrated in vacuo. The resulting oil was partitioned between CHCl$_3$ and 1N NaOH. The aqueous phase was extracted again with CHCl$_3$. The combined organics were washed with 1N NaOH, dried over MgSO$_4$, filtered and concentrated in vacuo to yield a brown oil (23.8 mmol). The crude product was purified by flash chromatography (SiO$_2$) eluting with 5% MeOH/CHCl$_3$ to yield a yellow waxy solid (13 mmol, 2.7 g, 52%).

Anal. Calcd. for C$_{14}$H$_{18}$N$_2$.0.15 mol H$_2$O:C, 77.49; H, 8.50; N, 12.91.

Found: C, 77.13; H, 8.07; N, 12.77.

MS ((+)APCI, m/e(%)) 215(100, [M+H]$^+$).

IR (solid ATR, cm$^{-1}$) 3210, 2910, 2860, 2810, 1590, 1460, 1430, 1340, 1290, 750.

$^1$H NMR (DMSO-d$_6$, 400 MHz) δ 6.85(d, J=7.3 Hz, 1H), 6.72(d, J=7.1 Hz, 1H), 6.52(t, J=7.3 Hz, 1H), 3.89(m, 1H), 3.8, 3.48(ABq, J$_{AB}$=15.13 Hz, 2H), 3.69(dt, J=2.9 Hz, 1H), 3.08(m, 2H), 2.71 (m, 1H), 2.62(m, 1H), 2.29(br m, 1H), 1.90(m, 1H), 1.76(m, 1H), 1.68-1.48(m, 3H), 1.40(m, 1H).

EXAMPLE 2 rel-(4S,7bS,10aS)-4-Methyl-1,2,3,4,8,9,10,10a-Octahydro-7bH-Cyclopenta[b][4]Diazepino[6,7,1-hi]Indole 2-(2,3,3a,8b-tetrahydrocyclopenta[b]indol-4(1)-yl)ethylamine (4.9 mmol, 1.0 g) was dissolved in ethanol (25 mL) at room temperature and trifluoroacetic acid (4.9 mmol, 380 μL) was added, followed by acetaldehyde (4.9 mmol, 37%, 280 μL). The reaction was heated to reflux overnight. The reaction vessel was cooled and then concentrated in vacuo. The resulting oil was partitioned between CHCl$_3$ and 1N NaOH. The aqueous phase was extracted again with CHCl$_3$. The combined organics were washed with 1N NaOH, dried over MgSO$_4$, filtered and concentrated in vacuo to yield a brown oil (23.8 mmol). The crude product was purified by flash chromatography (SiO$_2$) eluting with 10% MeOH/CHCl$_3$ to give the two racemic diastereomers.

Less Polar Product:

Rf 0.5 (A) 10% Et$_3$N/EtOAc

MS ((+)APCI, m/e(%)) 229(100, [M+H]$^+$).

IR (film ATR, cm$^{-1}$) 2940, 2860, 1600, 1460, 1430, 1330, 1300, 1230, 1070, 750.

$^1$H NMR (DMSO-d$_6$, 400 MHz) δ 6.88(d, J=7.3 Hz, 1H), 6.81 (d, J=7.8 Hz, 1H), 6.59(t, J=7.4 Hz, 1H), 3.87(m, 1H), 3.71 (m, 1H), 3.45(q, J=6.7 Hz, 1H), 3.06(m, 2H), 2.80-2.67(m, 2H), 2.05(br m, 1H), 1.90(m, 1H), 1.75(m, 1H), 1.64(m, 1H), 1.52(m, 2H), 1.37 (m, 1H), 1.37(d, J=6.8 Hz, 3H).

EXAMPLE 3 rel-(4R,7bS,10aS)-4-Methyl-1,2,3,4,8,9,10,10a-Octahydro-7bH-Cyclopenta[b][1,4]Diazepino[6,7,1-hi]Indole Prepared in Example 2 isolating the more polar product.

Rf 0.39 (B) 10% Et$_3$N/EtOAc

MS ((+)APCI, m/e(%)) 229(100, [M+H]$^+$).

IR (film ATR, cm$^{-1}$) 2950, 2930, 2860, 1600, 1460, 1430, 1320, 1230, 1050, 750.

$^1$H NMR (DMSO-d$_6$, 400 MHz) δ6.81(d, J=7.1 Hz, 1H), 6.71(d, J=7.6 Hz, 1H), 6.52(t, J=7.3 Hz, 1H), 4.0(q, J=6.9 Hz, 1H), 3.82(dd, J=4.7 Hz, 8.6 Hz, 1H), 3.68(dt, J=2.7 Hz, 8.9 Hz, 1H), 3.05(m, 2H), 2.82-2.70(m, 2H), 2.3(br m, 1H), 1.88(m, 1H), 1.78(m, 1H), 1.64-1.48(m, 3H), 1.40(m, 1H), 1.17(d, J=7.1 Hz, 3H).

What is claimed:

1. A compound of the formula:

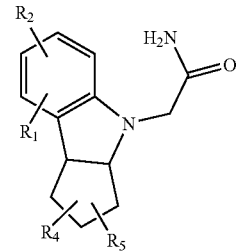

wherein R$_1$, R$_2$, R$_4$ and R$_5$ are each, independently, hydrogen, hydroxy, alkyl of 1-6 carbon atoms, cycloalkyl, alkoxy of 1-6 carbon atoms, halogen, fluorinated alkyl of from 1 to 6 carbon atoms, —CN, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl or aroyl.

2. A compound of claim 1 wherein R$_1$ and R$_2$ are hydrogen, and R$_4$ and R$_5$ are as defined in claim 1.

3. A compound of claim 1 wherein R$_1$, R$_2$ and R$_4$ are hydrogen, and R$_5$ is as defined in claim 1.

4. A compound of claim 1 which is 2-(2,3,3a,8b-Tetrahydro-1H-cyclopenta[b]indol-4-yl)-acetamide.

5. A compound of the formula:

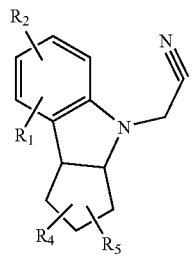

wherein $R_1$, $R_2$, $R_4$ and $R_5$ are each, independently, hydrogen, hydroxy, alkyl of 1-6 carbon atoms, cycloalkyl, alkoxy of 1-6 carbon atoms, halogen, fluorinated alkyl of from 1 to 6 carbon atoms, —CN, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl or aroyl.

6. A compound of claim 5 wherein $R_1$ and $R_2$ are hydrogen, and $R_4$ and $R_5$ are as defined in claim 1.

7. A compound of claim 5 wherein $R_1$, $R_2$ and $R_4$ are hydrogen, and $R_5$ is as defined in claim 1.

8. A compound of claim 5 which is 2-(2,3,3a,8b-Tetrahydro-1H-cyclopenta[b]indol-4-yl)-acetonitrile.

9. A compound of the formula:

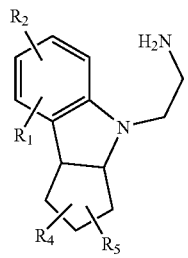

wherein $R_1$, $R_2$, $R_4$ and $R_5$ are each, independently, hydrogen, hydroxy, alkyl of 1-6 carbon atoms, cycloalkyl, alkoxy of 1-6 carbon atoms, halogen, fluorinated alkyl of from 1 to 6 carbon atoms, —CN, —NH—SO$_2$-alkyl of 1-6 carbon atoms, —SO$_2$—NH-alkyl of 1-6 carbon atoms, alkyl amide of 1-6 carbon atoms, amino, alkylamino of 1-6 carbon atoms, dialkylamino of 1-6 carbon atoms per alkyl moiety, fluorinated alkoxy of 1-6 carbon atoms, acyl of 2-7 carbon atoms, aryl or aroyl.

10. A compound of claim 9 wherein $R_1$ and $R_2$ are hydrogen, and $R_4$ and $R_5$ are as defined in claim 1.

11. A compound of claim 9 wherein $R_1$, $R_2$ and $R_4$ are hydrogen, and $R_5$ is as defined in claim 1.

12. A compound of claim 9 which is 2-(2,3,3a,8b-Tetrahydro-1H-cyclopenta[b]indol-4-yl)-ethylamine.

* * * * *